(12) United States Patent
Ishizuka et al.

(10) Patent No.: US 11,047,849 B2
(45) Date of Patent: Jun. 29, 2021

(54) METHOD FOR OBSERVING SEBACEOUS GLAND AND USE THEREOF

(71) Applicant: MANDOM CORPORATION, Osaka (JP)

(72) Inventors: Shuta Ishizuka, Osaka (JP); Ryuichiro Kurata, Osaka (JP)

(73) Assignee: MANDOM CORPORATION, Osaka (JP)

( * ) Notice: Subject to any disclaimer, the term of this patent is extended or adjusted under 35 U.S.C. 154(b) by 0 days.

(21) Appl. No.: 16/769,719

(22) PCT Filed: Sep. 5, 2019

(86) PCT No.: PCT/JP2019/034898
§ 371 (c)(1),
(2) Date: Jun. 4, 2020

(87) PCT Pub. No.: WO2020/079981
PCT Pub. Date: Apr. 23, 2020

(65) Prior Publication Data
US 2020/0371090 A1   Nov. 26, 2020

(30) Foreign Application Priority Data

Oct. 17, 2018   (JP) .............................. JP2018-196079

(51) Int. Cl.
*G01N 33/50*   (2006.01)
*G01N 33/15*   (2006.01)
*G01N 1/28*    (2006.01)

(52) U.S. Cl.
CPC ......... *G01N 33/5082* (2013.01); *G01N 33/15* (2013.01); *G01N 1/28* (2013.01)

(58) Field of Classification Search
CPC ......... G01N 33/58082; G01N 33/5008; G01N 33/15; G01N 1/28
See application file for complete search history.

(56) References Cited

U.S. PATENT DOCUMENTS 5,514,555 A  *  5/1996  Springer ................. A61P 37/00
                                                 435/7.24
10,036,741 B2 *  7/2018  Mills ..................... G01N 33/502
(Continued)

FOREIGN PATENT DOCUMENTS

JP      5-268949 A      10/1993
JP   2011-523548 A       8/2011
(Continued)

OTHER PUBLICATIONS

Zhongfa Lu et al., Towards the development of a simplified long-term organ culture method for human scalp skin and its appendages under serum-free conditions, Experimental Dermatology, vol. 16, 2007. (Year: 2007).*

(Continued)

*Primary Examiner* — David A. Rogers
(74) *Attorney, Agent, or Firm* — Westerman, Hattori, Daniels & Adrian, LLP

(57) ABSTRACT

Provided is a method for observing a sebaceous gland, the method making it possible to observe dynamics of a sebaceous gland which dynamics are close to dynamics of a sebaceous gland in a living body. The method includes: an anchoring step of anchoring a sebaceous gland structure to a support so that a sebaceous gland that is included in the sebaceous gland structure and is to be observed and the support are not in biological contact with each other, the sebaceous gland structure being obtained by removing all or part of each of dermis and hypodermis from a skin tissue; and an observation step of observing the sebaceous gland structure obtained in the anchoring step.

5 Claims, 5 Drawing Sheets

(56) References Cited

U.S. PATENT DOCUMENTS

| | | | |
|---|---|---|---|
| 2011/0150773 A1 | 6/2011 | Aubert et al. | |
| 2011/0151554 A1* | 6/2011 | Yuo | C12N 5/0634 435/363 |
| 2012/0003244 A1* | 1/2012 | Christiano | C07K 14/705 424/172.1 |
| 2015/0209428 A1* | 7/2015 | Imbert | A61P 17/00 514/410 |
| 2015/0268254 A1 | 9/2015 | Guasch et al. | |
| 2016/0145579 A1* | 5/2016 | Porat | C12N 5/0607 424/93.7 |
| 2016/0289624 A1* | 10/2016 | Totani | C12M 25/06 |
| 2016/0317528 A1* | 11/2016 | Koizumi | A61P 27/02 |
| 2016/0326486 A1* | 11/2016 | Fan | A61L 27/08 |
| 2017/0029779 A1* | 2/2017 | Zhang | C12N 5/0629 |
| 2019/0049429 A1 | 2/2019 | Nakashima et al. | |
| 2019/0201579 A1 | 7/2019 | Tsuji et al. | |

FOREIGN PATENT DOCUMENTS

| | | | | |
|---|---|---|---|---|
| JP | 2013-32331 A | | 2/2013 | |
| JP | 2015-530122 A | | 10/2015 | |
| KR | 20100007730 A | * | 1/2010 | ........... C12N 5/0623 |
| WO | 2017/221870 A1 | | 12/2017 | |
| WO | 2018/016501 A1 | | 1/2018 | |
| WO | 2018/114784 A1 | | 6/2018 | |

OTHER PUBLICATIONS

International Search Report dated Nov. 5, 2019, issued in counterpart International Application No. PCT/JP2019/034898 (2 pages).
Decision to Grant a Patent dated Apr. 14, 2020, issued in counterpart JP Patent Application No. 2020-504739, w/ English translation (5 pages).

* cited by examiner

METHOD FOR OBSERVING SEBACEOUS GLAND AND USE THEREOF

TECHNICAL FIELD

The present invention relates to a method for observing a sebaceous gland. The present invention also relates to (i) a sample for observation of a sebaceous gland (hereinafter referred to as a "sebaceous gland observation sample") and (ii) a method for evaluating, with use of the sample, a sebum production regulating action possessed by a test substance.

BACKGROUND ART

Sebum is secreted from a sebaceous gland into a surface of skin and has a function of protecting the skin from a stimulus from outside a body. In order to keep the skin healthy, moderate secretion of sebum in proper quantities is important. Thus, an external preparation (e.g., a cosmetic) that moderately regulates production of sebum is being desired.

Examples of a known method for analyzing an influence of a substance on production of sebum include a method in which a sebaceous gland cell is cultured in a medium containing a test substance and an amount of lipid in the sebaceous gland cell is measured (see Patent Literature 1).

Furthermore, a method for observing dynamics of a sweat gland, which is also an exocrine gland as is the case with a sebaceous gland, the dynamics being close to dynamics of a sweat gland in a living body, has been reported. For example, Patent Literature 2 discloses (a) a method of coating, with biological substrate gel, a sweat gland isolated from a skin tissue, (b) a method of adhering the sweat gland to a support with use of a biological substrate, (c) a method of placing a membrane on the sweat gland so as to anchor the sweat gland, and (d) the like method. Such a method makes it possible to prevent a sweat gland from being positionally displaced in a vessel. This results in achievement of accurate observation of dynamics of a sweat gland.

CITATION LIST

Patent Literatures

[Patent Literature 1]
Japanese Patent Application Publication Tokukai No. 2013-32331
[Patent Literature 2]
International Publication No. WO 2018/016501

SUMMARY OF INVENTION

Technical Problem

Note, however, that production of sebum from a sebaceous gland in a living body is insufficiently reproduced according to the method disclosed in Patent Literature 1. This makes it impossible to accurately observe dynamics of a sebaceous gland which dynamics are close to dynamics of a sebaceous gland in a living body.

Note also that application of the method disclosed in Patent Literature 2 for observing dynamics of a sweat gland to a sebaceous gland has not been studied.

An aspect of the present invention has an object to provide (i) a method for observing a sebaceous gland, the method allowing observation of dynamics of a sebaceous gland which dynamics are close to dynamics of a sebaceous gland in a living body, and (ii) a technique for using the method.

Solution to Problem

In order to attain the object, the inventors of the present invention repeatedly carried out diligent study. As a result, the inventors of the present invention succeeded, for the first time, in observing dynamics of a sebaceous gland in an anchored state by anchoring a sebaceous gland structure to a support under the condition that a sebaceous gland that is included in the sebaceous gland structure and is to be observed and the support are not in biological contact with each other. The inventors of the present invention obtained knowledge that the dynamics of a sebaceous gland thus observed are close to dynamics of a sebaceous gland in a living body. The inventors of the present invention finally accomplished the present invention based on the knowledge.

Specifically, an aspect of the present invention relates to a method for observing a sebaceous gland, including: an anchoring step of anchoring a sebaceous gland structure to a support so that a sebaceous gland that is included in the sebaceous gland structure and is to be observed and the support are not in biological contact with each other, the sebaceous gland structure being obtained by removing all or part of each of dermis and hypodermis from a skin tissue; and an observation step of observing the sebaceous gland structure obtained in the anchoring step.

Furthermore, another aspect of the present invention relates to a sebaceous gland observation sample including: a sebaceous gland structure obtained by removing all or part of each of dermis and hypodermis from a skin tissue; a support; and an anchoring member, the sebaceous gland structure being anchored to the support via the anchoring member so that a sebaceous gland that is included in the sebaceous gland structure and is to be observed and the support are not in biological contact with each other.

Advantageous Effects of Invention

An aspect of the present invention makes it possible to provide a method for observing a sebaceous gland, the method allowing observation of dynamics of a sebaceous gland which dynamics are close to dynamics of a sebaceous gland in a living body.

BRIEF DESCRIPTION OF DRAWINGS

In FIG. 4, a part enclosed by a dotted line indicates a position of sebum.

In FIG. 5, a part enclosed by a dotted line indicates a position of a nucleus.

In FIG. 6, a part enclosed by a dotted line indicates a position of a nucleus.

DESCRIPTION OF EMBODIMENTS

Figure 1:
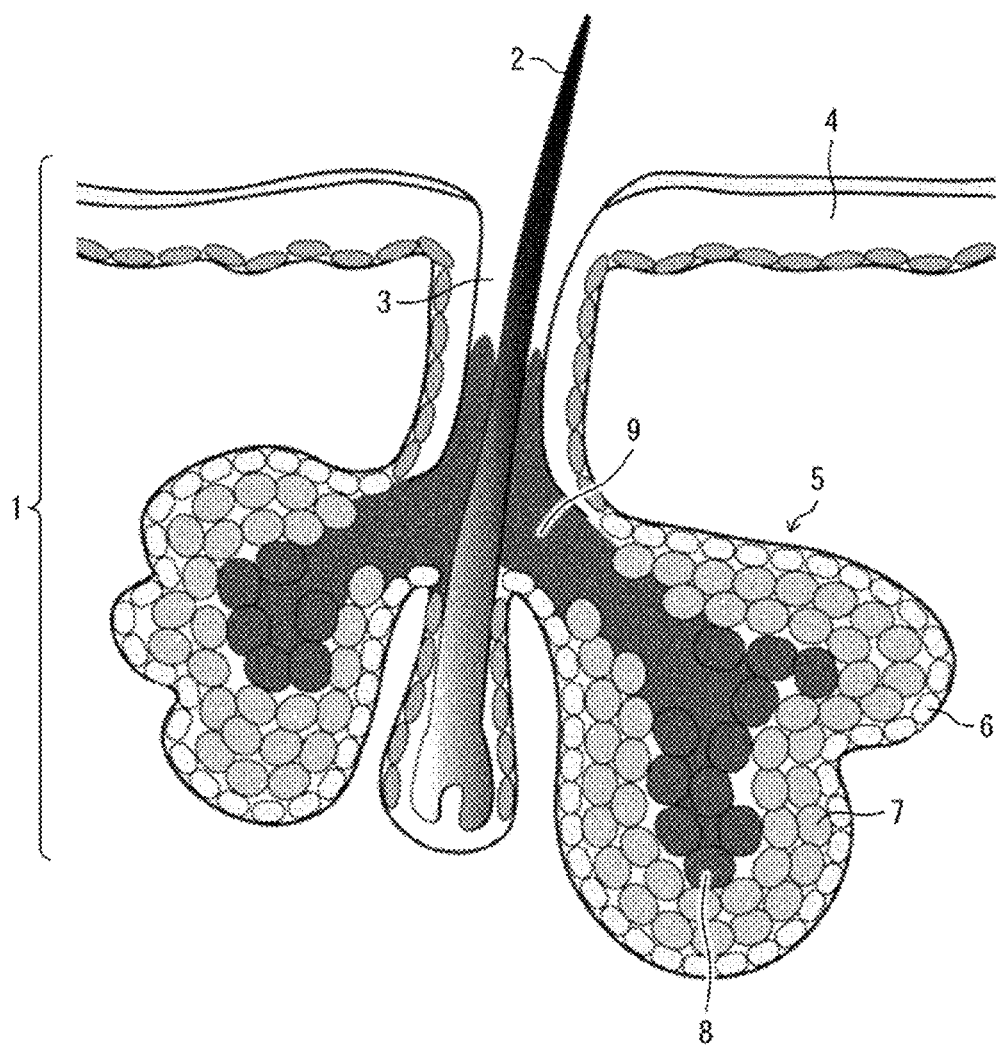
FIG. 1 is a view schematically illustrating a structure of a main part of a sebaceous gland structure which main part includes a sebaceous gland.

The following description will discuss an embodiment of the present invention. The present invention is, however, not limited to the embodiment below. The present invention is not limited to arrangements described below, and may be altered in various ways by a skilled person within the scope of the claims. Any embodiment derived from a proper combination of technical means disclosed in different embodiments is also encompassed in the technical scope of the present invention. Note that numerical expressions such as "A to B" herein mean "not less than A and not more than B" unless otherwise specified.

1. Overview

A method in accordance with an embodiment of the present invention for observing a sebaceous gland (hereinafter referred to as "the present observation method") is a method including: an anchoring step (for convenience, hereinafter also referred to as a "step (I)") of anchoring a sebaceous gland structure to a support so that a sebaceous gland that is included in the sebaceous gland structure and is to be observed and the support are not in biological contact with each other, the sebaceous gland structure being obtained by removing all or part of each of dermis and hypodermis from a skin tissue; and an observation step (for convenience, hereinafter also referred to as a "step (II)") of observing the sebaceous gland structure obtained in the anchoring step.

In order to study a method for observing dynamics of a sebaceous gland, the inventors of the present invention considered first whether it is possible to apply the method disclosed in Patent Literature 2 (i.e., the method for observing dynamics of a sweat gland) to a sebaceous gland.

Note, however, that the inventors of the present invention uniquely found that application of the method disclosed in Patent Literature 2 to a sebaceous gland causes the following problems.

(i) Unlike an eccrine sweat gland (hereinafter referred to as a "sweat gland"), a sebaceous gland is an organ annexed to a hair follicle. Thus, in order to observe dynamics of a sebaceous gland which dynamics are close to dynamics of a sebaceous gland in a living body, it is necessary to observe not a sebaceous gland alone but a sebaceous gland that remains connected with each of epidermis and a hair follicle (i.e., in a state of a sebaceous gland structure). Note, however, that, it takes a sebaceous gland more time to respond to, for example, an external stimulus substance, as compared with a sweat gland. In this case, use of biological substrate gel or a biological substrate may (i) cause a cell to migrate to, for example, a biological substrate for use in anchoring over time and (ii) consequently cause a sebaceous gland structure to lose its intrinsic function.

(ii) In a sebaceous gland structure, a sebaceous gland contains therein a lot of oils and fats (sebum), and epidermis is hydrophobic. Thus, the sebaceous gland structure as a whole is highly buoyant. Therefore, even an attempt to anchor the sebaceous gland structure by placing thereon a membrane is insufficient to anchor the sebaceous gland structure. This results in floating of the sebaceous gland structure.

In order to solve the above problems, the inventors of the present invention further carried out study. As a result, the inventors of the present invention found, for the first time, that it is possible to observe dynamics of a sebaceous gland in an anchored state by anchoring a sebaceous gland structure to a support under the condition that a sebaceous gland that is included in the sebaceous gland structure and is to be observed and the support are not in biological contact with each other. The inventors of the present invention also found that the dynamics of a sebaceous gland thus observed sufficiently reproduce production of sebum from a sebaceous gland in a living body.

According to the present observation method, since it is possible to observe dynamics of a sebaceous gland in an anchored state and the dynamics of a sebaceous gland thus observed are close to dynamics of a sebaceous gland in a living body, it is possible to provide a method for observing dynamics of a sebaceous gland which dynamics are close to dynamics of a sebaceous gland in a living body. According to the present observation method, it is also possible to observe, over time, dynamics of a sebaceous gland which dynamics are close to dynamics of a sebaceous gland in a living body.

2. Observation Method

The present observation method is a method including: an anchoring step of anchoring a sebaceous gland structure to a support so that a sebaceous gland that is included in the sebaceous gland structure and is to be observed and the support are not in biological contact with each other, the sebaceous gland structure being obtained by removing all or part of each of dermis and hypodermis from a skin tissue; and an observation step of observing the sebaceous gland structure obtained in the anchoring step.

According to the present observation method, an operation to anchor a sebaceous gland structure to a support so that a sebaceous gland that is included in the sebaceous gland structure and is to be observed and the support are not in biological contact with each other is employed. Thus, even in a case where all or part of each of dermis and hypodermis is removed in the sebaceous gland structure, dynamics of a sebaceous gland in a living body which dynamics are typified by, for example, production of sebum from a sebaceous gland in a living body are accurately reproduced so as to be easily observed. Therefore, according to the present observation method, it is possible to observe dynamics of a sebaceous gland in an environment closer to an inside of a living body.

The "sebaceous gland structure" herein refers to a structure obtained by removing all or part of each of dermis and hypodermis from a skin tissue and includes at least a hair follicle and epidermis in addition to a sebaceous gland.

The sebaceous gland structure is similar in structure to a skin tissue in a living body except that all or part of each of dermis and hypodermis has been removed from a skin tissue in the sebaceous gland structure. Thus, the sebaceous gland structure is suitable for observation of dynamics of a sebaceous gland in an environment close to an inside of a living body. In the sebaceous gland structure, a sebaceous gland has a function of maintaining a connection between a hair follicle and epidermis.

The sebaceous gland structure can further include dermis and hypodermis in addition to the sebaceous gland, the epidermis, and the hair follicle.

The sebaceous gland structure can include a sebaceous gland(s) that are not particularly limited in number. The sebaceous gland structure can include one or more sebaceous glands. The sebaceous gland structure preferably includes five or more observable sebaceous glands so that a sebaceous gland that is more favorable for observation can be selected.

The sebaceous gland structure is specifically described below with reference to FIG. 1. Specifically, a sebaceous gland structure 1 includes a hair 2, a hair follicle 3 that surrounds the hair 2, epidermis 4, and a sebaceous gland 5 (see FIG. 1). The sebaceous gland 5 includes (i) sebaceous gland basal cells 6 that are undifferentiated and localized in an outermost layer of the sebaceous gland 5, (ii) cells (hereinafter also referred to as "differentiated sebaceous gland cells") 7 that generate lipid droplets (sebum) and are localized on an inner side than a place where the sebaceous gland basal cells 6 are localized, (iii) mature sebaceous gland cells 8 that are localized in a central part of the sebaceous gland 5 and have been swollen by accumulation of sebum by the differentiated sebaceous gland cells 7, and (iv) sebum 9 that has flowed out from an inside of the mature sebaceous gland cells 8 which died out and were destroyed. The sebum 9 that has been generated in the sebaceous gland 5 is released to an outside of skin via the hair follicle 3. A part of the sebaceous gland structure 1 which part is constituted by the sebaceous gland 5, the hair 2, the hair follicle 3, and the epidermis 4 is similar in structure to a part of a skin tissue in a living body which part is constituted by a sebaceous gland, a hair, and a hair follicle, except that all or part of each of dermis and hypodermis has been removed from a skin tissue in the sebaceous gland structure 1.

Note that the expression "all or part of each of dermis and hypodermis has been removed from a skin tissue" herein means that dermis and hypodermis have been removed from a skin tissue and a sebaceous gland is exposed enough to be observable.

In the step (I), a sebaceous gland structure is anchored to a support so that a sebaceous gland that is included in the sebaceous gland structure and is to be observed and the support are not in biological contact with each other. The sebaceous gland structure can be produced by, for example, removing all or part of each of dermis and hypodermis from an isolated skin tissue. Thus, the present observation method can further include a step of obtaining, before carrying out the step (I), the sebaceous gland structure by removing all or part of each of dermis and hypodermis from an isolated skin tissue.

Examples of a method for producing the sebaceous gland structure include:

a method (hereinafter also referred to as a "production method A") including the steps of:
 (a1) removing all or part of hypodermis from an isolated skin tissue; and
 (a2) obtaining the sebaceous gland structure by removing, from a tissue obtained in the step (a1), a fiber such as a collagenous fiber so as to cause a sebaceous gland to be exposed; and a method (hereinafter also referred to as a "production method B") including the steps of:
 (b1) removing all or part of hypodermis from an isolated skin tissue;
 (b2) bringing a tissue obtained in the step (b1) into contact with an enzyme (e.g., dispase, collagenase, or pronase) for dissociating, from dermis, an organ annexed to epidermis; and
 (b3) separating the dermis from a tissue obtained in the step (b2). Note, however, that the present invention is not limited only to these examples. From the viewpoint that the sebaceous gland structure can be easily produced and dynamics of a sebaceous gland in a living body can be accurately observed, of such methods for producing the sebaceous gland structure, the production method A and the production method B are preferable, and the production method A is more preferable.

Examples of the isolated skin tissue include a skin tissue that is alive and has been obtained from, for example, an excess skin produced during a surgical operation. Note, however, that the present invention is not limited only to these examples. Note that the expression "a skin tissue that is alive" herein means a skin tissue that exhibits biological activity and behavior similar to intrinsic biological activity and intrinsic behavior, respectively, in a living body.

Examples of a source of supply of the skin tissue include a human. Note, however, that the present invention is not limited only to these examples. The source of supply of the skin tissue is preferably a human in a case where the present observation method is used to, for example, observe a sebaceous gland during production of sebum in a human. Since it has been conventionally difficult to accurately observe dynamics of a sebaceous gland of a human, the present observation method is suitable for observation of a sebaceous gland of a human.

Examples of dynamics of a sebaceous gland include (i) a change in shape of cells in a case where shapes, obtained at two or more time points during production of sebum, of the cells constituting a sebaceous gland are compared; (ii) a change in differentiated state of cells in a case where differentiated states, obtained at two or more time points during production of sebum, of the cells constituting a sebaceous gland are compared; (iii) a change in shape of differentiated cells in a case where shapes, obtained at two or more time points during production of sebum, of the differentiated cells are compared; and (iv) a change in position of localized sites of differentiated cells in a case where positions, obtained at two or more time points during production of sebum, of the localized sites of the differentiated cells are compared. Note, however, that the present invention is not limited only to these examples.

In the step (I) of the present observation method, a sebaceous gland structure is anchored to a support so that a sebaceous gland that is included in the sebaceous gland structure and is to be observed and the support are not in biological contact with each other.

The expression "a sebaceous gland and a support are not in biological contact with each other" herein means that a sebaceous gland is not under a biological influence by a contact with the support via a biological substrate. Examples of the biological influence include migration of a cell in a sebaceous gland into a biological substrate or a medium, destruction of unity of the sebaceous gland structure, and differentiation of a sebaceous gland cell. Thus, a case where a sebaceous gland and a support are in physical contact with each other but the sebaceous gland is not under the biological influence is encompassed in the scope of the definition of "a sebaceous gland and a support are not in biological contact with each other".

A sebaceous gland that is not in biological contact with the support is a sebaceous gland that is included in the sebaceous gland structure and is to be observed. A sebaceous gland that is not to be observed can be in biological contact with the support. The sebaceous gland structure that has a predetermined size (for example, measures 1 cm per side) commonly includes a plurality of sebaceous glands. In a case where, for example, a sebaceous gland located in a central part of the sebaceous gland structure is to be observed, a sebaceous gland located at an end of the sebaceous gland structure is not to be observed. This means that a sebaceous gland located at an end of the sebaceous gland structure can be in biological contact with the support provided that the sebaceous gland does not affect a sebaceous gland to be observed.

A sebaceous gland that is included in the sebaceous gland structure and is to be observed is preferably not in contact with the support, but may be alternatively preferably in contact, different from biological contact, with the support. For example, a sebaceous gland that is in contact with the support may be advantageous (e.g., easy to observe or observable with high accuracy) depending an observation device (e.g., a microscope) and/or a vessel to be used as the support (e.g., a culture vessel for culturing the sebaceous gland structure). In such a case, a sebaceous gland to be observed can be in contact, different from biological contact, with the support.

The support is not limited to any particular support provided that the support (i) is an object that allows the sebaceous gland structure to be anchored so that a sebaceous gland that is included in the sebaceous gland structure and is to be observed and the support are not in biological contact with each other and (ii) is suitable for the observation device. Examples of the support include vessels such as a laboratory dish, a dish, a plate, a flask, a chamber, and a tube. Preferable examples of a material of which the support is made include various materials such as common plastics and common glass. From the viewpoint that a sebaceous gland that is included in the sebaceous gland structure and is to be observed and the support are not in biological contact with each other, the support is preferably made of a material whose surface is not coated with a biological substrate.

According to an embodiment of the present invention, the sebaceous gland structure and the support are anchored to each other via a biological substrate in the step (I). The term "biological substrate" is herein also referred to as an "anchoring member" because the biological substrate is a material that acts as an intermediary for anchoring of the sebaceous gland structure and the support. The biological substrate is not limited to any particular biological substrate provided that the biological substrate can be joined to each of the sebaceous gland structure and the support so as to allow the sebaceous gland structure and the support to be anchored to each other. Examples of the biological substrate include collagen, agarose, a basement membrane matrix, and poly-D-lysine. Thus, according to an embodiment of the present invention, the sebaceous gland structure is anchored to the support via at least one material selected from the group consisting of collagen, agarose, a basement membrane matrix, and poly-D-lysine.

The collagen is exemplified by, but not limited to, type I collagen such as collagen type I-A and collagen type I-B; type III collagen; and type IV collagen.

The agarose can be agarose having a melting point, which is a temperature at which a cell constituting a sebaceous gland can survive.

The basement membrane matrix can contain laminin, collagen type IV, nidogen, and heparan sulfate proteoglycan as essential components. The basement membrane matrix is exemplified by, but not limited to, Matrigel Basement Membrane Matrix (manufactured by Corning).

The poly-D-lysine can have a molecular weight enough to adhere, to the support, a cell constituting a sebaceous gland.

According to an embodiment of the present invention, in the step (I), at least one tissue included in the sebaceous gland structure and selected from the group consisting of epidermis, a hair follicle, dermis, hypodermis, and a sebaceous gland different from the sebaceous gland to be observed is joined to the support via the biological substrate, so that the sebaceous gland structure and the support are anchored to each other.

The expression "anchored to the support so that a sebaceous gland that is included in the sebaceous gland structure and is to be observed and the support are not in biological contact with each other" herein means that the sebaceous gland structure is anchored to the support so that a sebaceous gland to be observed is not under the biological influence by a contact with the support via the biological substrate. The sebaceous gland structure thus anchored does not move on the support during observation and is therefore suitable for observation.

According to an embodiment of the present invention, the sebaceous gland structure to be anchored can have any shape and any size that are not particularly limited. For example, from the viewpoint of easiness of operation, the sebaceous gland structure is preferably a sebaceous gland structure that has been prepared so as to be a quadrangle measuring 3 mm to 5 mm per side.

It is also not particularly limited how the sebaceous gland structure is anchored on the support. Note, however, that, in order that a medium can be in contact with a sebaceous gland included in the sebaceous gland structure, it is undesirable that all ends of the sebaceous gland structure be anchored to the support. Specifically, at least one of the ends of the sebaceous gland structure is preferably unanchored to the support. For example, in a case where the sebaceous gland structure is quadrangular, a pair of both ends (i.e., two ends) that are included in the four ends and are opposite to each other can be anchored.

The expression "a sebaceous gland included in the sebaceous gland structure" herein means sebaceous gland that is included in the sebaceous gland structure and arbitrarily selected so that dynamics of a sebaceous gland are observed.

As a sebaceous gland to be observed, a sebaceous gland that is not in biological contact with the support can be selected, as appropriate, from the sebaceous gland structure. For example, since a sebaceous gland present near an end of the sebaceous gland structure is highly likely to be in biological contact with the biological substrate, a sebaceous gland present near the central part of the sebaceous gland structure is preferably to be observed.

In another embodiment of the present invention, by placing a weight material such as a membrane on the sebaceous gland structure so as to anchor the membrane and the support, it is alternatively possible to anchor the sebaceous gland structure to the support so that a sebaceous gland that is included in the sebaceous gland structure and is to be observed and the support are not in biological contact with each other. In this case, the membrane can be anchored to the support via, for example, the biological substrate.

The membrane can be a membrane that has pores whose pore diameter allows a buffer, a test substance (described later), and the like to be passed through the pores while preventing the sebaceous gland structure from being passed through the pores. The pore diameter is preferably not more than 5 mm, and more preferably not more than 1 mm, in order to prevent or reduce passage of a sebaceous gland, and is preferably not less than 0.1 µm in order to allow passage of a test substance (described later).

In the step (I), a medium is added so that the sebaceous gland structure anchored to the support is cultured in the medium. The sebaceous gland structure that is cultured in the medium can maintain its living state. This makes it possible to observe dynamics of a sebaceous gland in an environment closer to an inside of a living body.

The medium can be a medium containing (i) a differentiation promoting component suitable for differentiating, into a mature sebaceous gland cell, an undifferentiated sebaceous gland basal cell included in the sebaceous gland structure and (ii) a growth component for causing cell growth. The medium is not limited to any particular medium. The medium can alternatively be a medium obtained by supplementing a conventional basal medium with the differentiation promoting component and the growth component. Alternatively, the medium can be a commercially-available medium. Examples of the differentiation promoting component include fetal bovine serum, fatty acid, peptide, and hormone. Note, however, that the present invention is not limited only to these examples. These differentiation promoting components can be used alone or in combination of two or more kinds. A differentiation promoting component content in the medium is not absolutely determined because the differentiation promoting component content varies depending on, for example, a kind of the medium and/or a kind of the differentiation promoting component. Thus, the differentiation promoting component content is preferably set as appropriate in accordance with, for example, a kind of the medium and/or a kind of the differentiation promoting component. Examples of the growth component include an amino acid, a vitamin, an inorganic salt, a saccharide, and a cell growth promoting factor. Note, however, that the present invention is not limited only to these examples. A growth component content in the medium is not absolutely determined because the growth component content varies depending on, for example, a kind of the medium and/or a kind of the growth component. Thus, the growth component content is preferably set as appropriate in accordance with, for example, a kind of the medium and/or a kind of the growth component. These growth components can be used alone or in combination of two or more kinds. Examples of the basal medium include a mixed medium of a Dulbecco's modified medium and an F-12 medium. Note, however, that the present invention is not limited only to these examples.

A culture condition under which to culture the sebaceous gland structure cannot be absolutely determined because the culture condition varies depending on, for example, a kind of a source of supply of a skin tissue for use in production of the sebaceous gland structure and/or a kind of dynamics of a sebaceous gland to be observed. Thus, the culture condition is desirably determined in accordance with, for example, a kind of a source of supply of a skin tissue for use in production of the sebaceous gland structure and/or a kind of dynamics of a sebaceous gland to be observed. Examples of the culture condition include a culture temperature, a culture time, pH of a medium, and a carbon dioxide concentration in a culture atmosphere.

In a case where a source of supply of the skin tissue is a human, a culture temperature is ordinarily preferably 35° C. to 38° C., and more preferably 36.5° C. to 37.5° C., in order to accurately reproduce a state of a sebaceous gland in a living body. Furthermore, in a case where a source of supply of the skin tissue is a human, a culture time is ordinarily preferably 6 hours to 168 hours, and more preferably 24 hours to 48 hours, in order to maintain a physiological function of the sebaceous gland structure in a favorable state in the medium. Moreover, in a case where a source of supply of the skin tissue is a human, pH of the medium is ordinarily preferably 6.8 to 7.6, and more preferably 7.0 to 7.4, in order to accurately reproduce a state of a sebaceous gland in a living body. A carbon dioxide concentration in a culture atmosphere is ordinarily preferably 4% by volume to 10% by volume, and more preferably 5% by volume to 7% by volume, in order to accurately reproduce a state of a sebaceous gland in a living body.

Subsequently, in the step (II), the sebaceous gland structure obtained in the step (I) is observed. The sebaceous gland structure can be observed by, for example, (i) using, as an observation sample, the sebaceous gland structure that has been stained with a staining reagent before the step (I) or (ii) using, as an observation sample, the sebaceous gland structure that has been stained with a staining reagent after the step (I).

The sebaceous gland structure can be stained by, for example, bringing the sebaceous gland structure and the staining reagent into contact with each other. Examples of the staining reagent include (i) a reagent containing a complex of (a) a binding substance that binds to a marker and (b) a detectable substance and (ii) a reagent containing the binding substance and not containing the detectable substance. Note, however, that the present invention is not limited only to these examples. Note that the term "marker" herein means a substance serving as (i) an indicator of presence of a tissue, a cell, and/or the like included in the sebaceous gland structure or (ii) an indicator of, for example, a degree of cell differentiation.

The binding substance varies depending on, for example, an application of the present observation method. Thus, the binding substance, which cannot be absolutely determined, is preferably determined as appropriate in accordance with, for example, an application of a method for observing a sebaceous gland. Examples of the binding substance include an antibody that binds to the marker (hereinafter merely referred to as an "antibody") and a fragment thereof (hereinafter merely referred to as an "antibody fragment"), and a compound that binds to the marker. Note, however, that the present invention is not limited only to these examples. The antibody can be a polyclonal antibody or a monoclonal antibody. Of these antibodies, a monoclonal antibody is preferable due to its high specificity to the marker. Examples of the antibody fragment include an Fab fragment, an F(ab')$_2$ fragment, and a single-stranded antibody. Note, however, that the present invention is not limited only to these examples. The polyclonal antibody, the monoclonal antibody, and the antibody fragment each can be produced by a conventional method by using the marker as an antigen. The polyclonal antibody can be a polyclonal antibody that is commercially easily available, the monoclonal antibody can be a monoclonal antibody that is commercially easily available, and the antibody fragment can be an antibody fragment that is commercially easily available. The binding substance can be a substance that generates a detectable signal, or a substance that does not generate the detectable signal.

Examples of the detectable substance include a fluorescent substance and an enzyme. Note, however, that the present invention is not limited only to these examples. Examples of the fluorescent substance include fluorescein isothiocyanate and the Alexa Fluor series of fluorescent substance (e.g., Alexa Fluor 647 (trade name) manufactured by Invitrogen Corporation). Note, however, that the present invention is not limited only to these examples. Examples of the enzyme include peroxidase and alkaline phosphatase. Note, however, that the present invention is not limited only to these examples. Of these detectable substances, a fluorescent substance is preferable because the fluorescent substance makes it easy to carry out a detection operation and makes it possible to detect a detection target object with high accuracy, and the Alexa Fluor series of fluorescent substance (e.g., Alexa Fluor 647 (trade name) manufactured by Invitrogen Corporation) is more preferable.

In a case where the binding substance is an antibody or an antibody fragment thereof, the staining reagent can further contain, as appropriate, a labeling binding substance that binds to the antibody or the antibody fragment thereof. Examples of the labeling binding substance include a complex of (i) a second binding substance that binds to the binding substance and (ii) a labeling substance. Note, however, that the present invention is not limited only to these examples. Examples of the second binding substance include an antibody to immunogloblin which antibody is possessed by an animal immunized during production of the antibody (i.e., the binding substance) and an antibody to a fragment of the immunogloblin. Note, however, that the present invention is not limited only to these examples. Examples of the labeling substance include the detectable substance. Note, however, that the present invention is not limited only to these examples.

A kind of the staining reagent cannot be absolutely determined because the kind varies depending on, for example, an application of a method for observing a sebaceous gland of an invention. Thus, the kind is preferably determined as appropriate in accordance with, for example, an application of a method for observing a sebaceous gland. Examples of the staining reagent include a staining reagent for the undifferentiated sebaceous gland basal cell (hereinafter also referred to as a "undifferentiated cell staining reagent"), a staining reagent for sebum (hereinafter also referred to as a "sebum staining reagent"), a staining reagent for a cell nucleus (hereinafter also referred to as a "nucleus staining reagent"), and a differentiated cell staining reagent. Note, however, that the present invention is not limited only to these examples.

The undifferentiated cell staining reagent contains a substance (hereinafter also referred to as an "undifferentiated cell binding substance") that binds to a marker (hereinafter also referred to as an "undifferentiated marker") specific to the undifferentiated sebaceous gland basal cell. The undifferentiated cell staining reagent can be a reagent containing a complex of an undifferentiated cell binding substance and a detectable substance. In a case where the undifferentiated cell binding substance per se is a substance that generates a detectable signal, the undifferentiated cell staining reagent can be a reagent containing the undifferentiated cell binding substance and not containing the detectable substance. The undifferentiated cell marker is exemplified by, but not particularly limited to, keratin-5, keratin-7, keratin-14, B lymphocyte-induced maturation protein-1 (Blimp1), and leucine-rich repeat and immunoglobulin-like domain protein-1 (Lrig1).

The nucleus staining reagent contains a binding substance (hereinafter also referred to as a "nucleus binding substance") that binds to a substance constituting a nucleus. The nucleus staining reagent can be a reagent containing a complex of a nucleus binding substance and a detectable substance. In a case where the nucleus binding substance per se is a substance that generates a detectable signal, the nucleus staining reagent can be a reagent containing the nucleus binding substance and not containing the detectable substance. Examples of the substance constituting a nucleus include a nucleic acid such as DNA. Note, however, that the present invention is not limited only to these examples. The nucleus binding substance can be a substance to be transmitted through a cell membrane. Examples of the nucleus binding substance include Hoechst 33342. Note, however, that the present invention is not limited only to these examples. Given that Hoechst 33342 is a substance that generates detectable fluorescence, the nucleus staining reagent can be a reagent not containing the detectable substance.

Examples of the sebum staining reagent include a liposoluble dye that is soluble in sebum. Note, however, that the present invention is not limited only to these examples. Examples of the liposoluble dye include Nile Red, Nile Blue, Oil Red O, Sudan III, Sudan IV, and Sudan Black B. Note, however, that the present invention is not limited only to these examples. Given that the liposoluble dye is dissolved in sebum so that the sebum is stained with the liposoluble dye, the sebum staining reagent containing the liposoluble dye can be a reagent not containing the detectable substance.

The differentiated cell staining reagent contains, for example, a substance (hereinafter also referred to as a "differentiated cell binding substance") that binds to a marker (hereinafter also referred to as a "differentiated marker") specific to the sebaceous gland basal cell into which the undifferentiated sebaceous gland basal cell has been differentiated. The differentiated cell staining reagent can be a reagent containing a complex of a differentiated cell binding substance and a detectable substance. In a case where the differentiated cell binding substance per se is a substance that generates a detectable signal, the differentiated cell staining reagent can be a reagent containing the differentiated cell binding substance and not containing the detectable substance. The differentiated cell marker is exemplified by, but not particularly limited to, stearoyl-CoA desaturase 1 (Scd-1) and peroxisome proliferator-activated receptor γ (PPARγ).

A binding substance content in the staining reagent is not absolutely determined because the binding substance content varies depending on, for example, a kind of the binding substance and/or an application of a method for observing a sebaceous gland of an invention. Thus, the binding substance content is preferably determined as appropriate in accordance with, for example, a kind of the binding substance and/or an application of a method for observing a sebaceous gland of an invention.

A detectable substance contained in the undifferentiated cell staining reagent, a detectable substance contained in the sebum staining reagent, and a detectable substance contained in the nucleus staining reagent are preferably substances that can be distinguished from each other.

A mixing ratio between the sebaceous gland structure and the staining reagent and a time for which the sebaceous gland structure and the staining reagent are in contact with each other are not absolutely determined because the mixing ratio and the time each vary depending on, for example, a kind of the staining reagent. Thus, the mixing ratio and the time are each preferably determined as appropriate in accordance with, for example, a kind of the staining reagent.

After the sebaceous gland structure and the staining reagent are in contact with each other, the sebaceous gland structure stained is preferably cleaned with an appropriate cleaning liquid so that dynamics of a sebaceous gland will be more accurately observed. Examples of the cleaning liquid include phosphate buffered physiological saline and a phosphate buffer. Note, however, that the present invention is not limited only to these examples.

In a case where the staining reagent contains an antibody or an antibody fragment thereof, the sebaceous gland structure stained is preferably subjected to a blocking treatment, carried out with use of a blocking agent, so that dynamics of a sebaceous gland will be more accurately observed. Examples of the blocking agent include a phosphate buffered physiological saline solution containing albumin. Note, however, that the present invention is not limited only to these examples.

The sebaceous gland structure stained is used to observe dynamics of a sebaceous gland. A sebaceous gland can be observed with use of, for example, an optical microscope such as a fluorescence microscope or a confocal laser scanning microscope. Specifically, observation of a sebaceous gland can be carried out by, for example, (i) observing, as it is, the sebaceous gland structure stained or (ii) detecting a staining reagent-derived signal in the sebaceous gland structure stained.

According to an embodiment of the present invention, the sebaceous gland structure can be observed from either a pore/epidermis side or a sebaceous gland side of the sebaceous gland structure. The sebaceous gland structure is observed preferably from the sebaceous gland side. For example, with reference to FIG. 2, the sebaceous gland structure can be observed from a side on which a support 12 is located (the sebaceous gland side) (specifically, the sebaceous gland structure can be observed from below the support 12).

As described above, the present observation method, which makes it possible to accurately observe production of sebum from a sebaceous gland, is expected to be used to, for example, screen sebaceous gland production regulating substances and evaluate efficacy of a sebaceous gland production regulating substance.

3. Sebaceous Gland Observation Sample

A sebaceous gland observation sample in accordance with an embodiment of the present invention (hereinafter referred to as "the present sample") includes: a sebaceous gland structure obtained by removing all or part of each of dermis and hypodermis from a skin tissue; a support; and an anchoring member, the sebaceous gland structure being anchored to the support via the anchoring member so that a sebaceous gland that is included in the sebaceous gland structure and is to be observed and the support are not in biological contact with each other.

Figure 2:
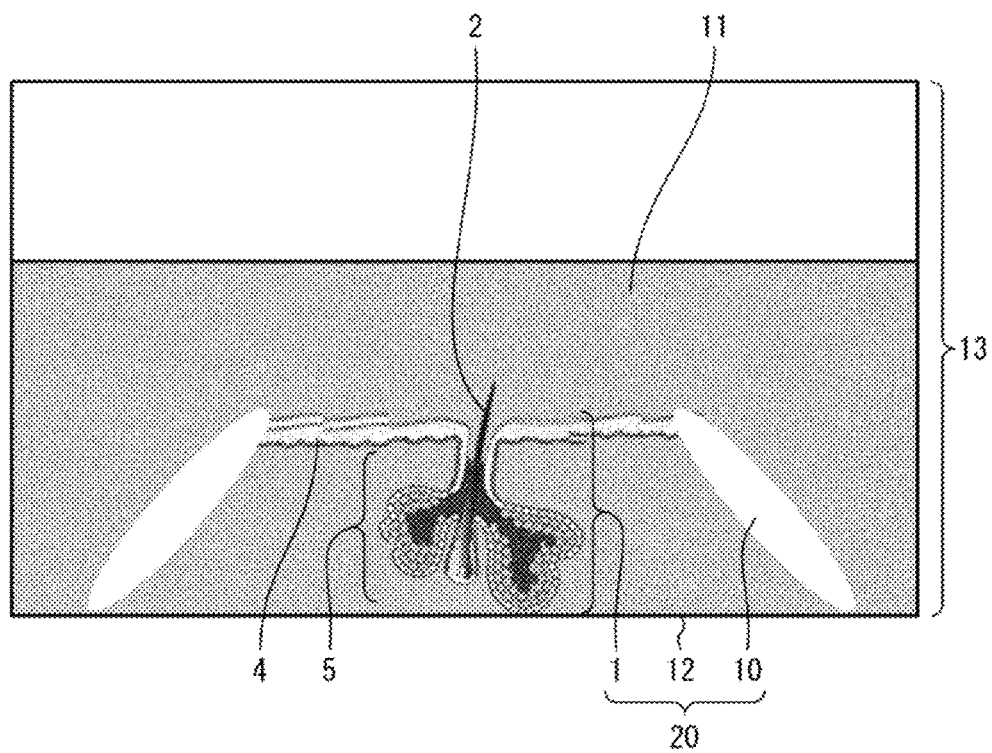
FIG. 2 is a view schematically illustrating an example of an aspect in which a sebaceous gland structure is anchored to a support in an observation method in accordance with an embodiment of the present invention.

The present sample is described below with reference to FIG. 2, which schematically illustrates the present sample. The present sample 20 includes the sebaceous gland structure 1, the support 12, and the biological substrate (anchoring member) 10. The sebaceous gland structure 1 is cultured in a medium 11 in a vessel 13. In FIG. 2, a bottom part of the vessel 13 functions as the support 12. Note, however, that a configuration of the support 12 is not limited to this. Alternatively, the support 12 can be a member that is provided separately from the vessel 13. The sebaceous gland structure 1 includes the hair 2, the epidermis 4, and the sebaceous gland 5 to be observed. The sebaceous gland structure 1 is anchored to the support 12 so that the epidermis 4 located at an end of the sebaceous gland structure 1 and the support 12 are anchored to each other via the biological substrate (anchoring member) 10. Note here that the sebaceous gland 5 to be observed is anchored so as not to be in biological contact with the support 12. That is, the sebaceous gland 5 to be observed is not in contact with the biological substrate (anchoring member) 10.

A sebaceous gland structure is commonly present in, for example, a medium in a vessel. Thus, the sebaceous gland structure that is not anchored with use of a biological substrate floats in the medium. This makes it impossible to observe the sebaceous gland structure. In contrast, the present sample 20 is anchored to the support 12 so that the sebaceous gland 5 of the sebaceous gland structure 1 is not in biological contact with the support 12. In particular, the sebaceous gland 5 is also not in contact with the biological substrate (anchoring member) 10. This prevents the sebaceous gland structure from being broken due to migration of a cell of the sebaceous gland 5. Thus, use of the present sample 20 makes it possible to accurately observe dynamics of a sebaceous gland which dynamics are close to dynamics of a sebaceous gland in a living body.

Since the sebaceous gland structure and the support of the present sample are identical to those described in [2. Observation method] above, the sebaceous gland structure and the support are specifically described with reference to [2. Observation method]. The sebaceous gland structure and the support of the present sample are anchored to each other in an aspect and by a method as described in [2. Observation method] above.

4. Method for Evaluating Test Substance

A method in accordance with an embodiment of the present invention for evaluating a sebum production regulating action possessed by a test substance (hereinafter referred to as "the present evaluation method") is a method including: a contact step of (for convenience, hereinafter referred to as a step (A)" of bringing a sebaceous gland observation sample into contact with a test substance; and an evaluation step (for convenience, hereinafter referred to as a "step (B)") of observing a sebaceous gland structure in the contact step so as to evaluate a sebum production regulating action of a test substance. Note that "contact with a test substance" can be an aspect in which a test substance and a sebaceous gland structure are in contact with each other. For example, it is possible to apply various methods such as an aspect in which a sebaceous gland structure is cultured in the presence of a test substance and an aspect in which a test substance is sprinkled directly on a sebaceous gland structure. The following description takes, as an example, a case where a sebaceous gland structure is cultured in a culture solution containing a test substance.

According to the present evaluation method, a sebaceous gland observation sample that is in contact with a test substance is observed. This makes it possible to evaluate, over time, a sebum production regulating action possessed by the test substance. Thus, the present evaluation method makes it possible to accurately evaluate whether a test substance is a substance that regulates production of sebum. The sebum production regulating action includes (i) a sebum production promoting action to increase sebum production and (ii) a sebum production reducing action to reduce sebum production.

In the step (A), the sebaceous gland observation sample is cultured in the presence of the test substance. The sebaceous gland observation sample that is used in the step (A) is similar to the present sample described in [3. Sebaceous gland observation sample] above. A medium that is used in the step (A) is similar to the medium described in [2.

Observation method] above. The sebaceous gland observation sample can be cultured in the step (A) by a method similar to the method, described in [2. Observation method] above, for culturing the sebaceous gland structure. A culture condition under which to culture the sebaceous gland observation sample cannot be absolutely determined because the culture condition varies depending on, for example, details of evaluation, a kind of a test substance to be evaluated, and/or a kind of a source of supply of a skin tissue for use in production of the sebaceous gland structure. Thus, the culture condition is desirably determined in accordance with, for example, details of evaluation, a kind of a test substance to be evaluated, and/or a kind of a source of supply of a skin tissue for use in production of the sebaceous gland structure.

In the step (B), the sebaceous gland structure in the step (A) is observed so that the sebum production regulating action of the test substance is evaluated.

For comparison, a step (C) of culturing the sebaceous gland observation sample in the absence of a test substance can also be carried out. A medium that is used in the step (C) and the medium that is used in the step (A) are identical in kind. In the step (C), the sebaceous gland observation sample can be cultured in the absence of a test substance by a method similar to the method, described in [2. Observation method] above, for culturing the sebaceous gland structure, except that a test substance-containing medium, for example is used in the step (C), the test substance-containing medium being obtained by adding a test substance to a medium whose kind is identical to that of the medium that is used in the step (A). A culture condition under which to culture the sebaceous gland observation sample in the step (C) and the culture condition under which to culture the sebaceous gland observation sample in the step (A) are identical except that no test substance is used in the step (C).

According to an embodiment of the present invention, a sebaceous gland observation sample (A) (hereinafter may also be referred to as a "sample (A)") cultured and obtained in the step (A) is observed, and a sebum production regulating action possessed by the test substance can be evaluated in accordance with a difference between dynamics of a sebaceous gland in the sebaceous gland observation sample (A) and dynamics of a sebaceous gland in an ordinary sebaceous gland structure. In this case, the sebum production regulating action is evaluated in comparison with ordinary dynamics without use of any control.

According to another embodiment of the present invention, (i) a sebaceous gland observation sample (A) cultured and obtained in the step (A) and (ii) a sebaceous gland observation sample (C) (hereinafter may also be referred to as a "sample (C)") cultured and obtained in the step (C) are observed, and a sebum production regulating action possessed by the test substance can be evaluated in accordance with a difference between dynamics of a sebaceous gland in the sebaceous gland observation sample (A) and dynamics of a sebaceous gland in the sebaceous gland observation sample (C).

According to a further embodiment of the present invention, a sebaceous gland observation sample (C) cultured and obtained in the step (C) is observed, the step (A) is carried out with use of a sample identical to the sample (C), a sample (A) thus obtained is observed, and then a sebum production regulating action possessed by the test substance can be evaluated in accordance with a difference between dynamics of a sebaceous gland in the sebaceous gland observation sample (C) cultured and obtained in the step (C) and dynamics of a sebaceous gland in the sample (A).

In a case where the step (C) is carried out, the step (A) and the step (C) can be carried out such that the step (A) is carried out and then the step (C) is carried out, or such that the step (C) is carried out and then the step (A) is carried out. Alternatively, the step (A) and the step (C) can be concurrently carried out.

Examples of a difference between dynamics of a sebaceous gland in the sebaceous gland observation sample (A) and dynamics of a sebaceous gland in an ordinary sebaceous gland structure or dynamics of a sebaceous gland in the sebaceous gland observation sample (C) include (i) a difference, caused by presence or absence of a test substance, in dynamics of cells that encapsulate sebum and are located in an outermost layer of a sebaceous gland; (ii) a difference, caused by presence or absence of a test substance, in speed of differentiation from an undifferentiated sebaceous gland basal cell into a mature sebaceous gland cell in a sebaceous gland; (iii) a difference, caused by presence or absence of a test substance, in dynamics of mature sebaceous gland cells that have been destroyed and are present near a central part of a sebaceous gland; (iv) a difference, caused by presence or absence of a test substance, in change in amount of sebum present in a central part of a sebaceous gland; (v) a difference, caused by presence or absence of a test substance, in change in position at which a differentiated marker is expressed; and (vi) a difference, caused by presence or absence of a test substance, in change in amount of expression of a differentiated marker. Note, however, that the present invention is not limited only to these examples.

An indication that the test substance has a sebum production promoting action cannot be absolutely determined because the indication varies depending on, for example, a kind of the test substance and/or a kind of a source of supply of a skin tissue for use in production of the sebaceous gland structure. Note, however, that examples of the indication include the following indications (1a) to (3a). These indications can be used alone or in combination of two or more kinds.

(1a) an indication that cells that encapsulate sebum and are located in an outermost layer of a sebaceous gland of the sebaceous gland observation sample (A) are larger in number than cells that encapsulate sebum and are located in an outermost layer of a sebaceous gland of the sebaceous gland observation sample (C);

(2a) an indication that differentiation from an undifferentiated sebaceous gland basal cell into a mature sebaceous gland cell in a sebaceous gland of the sebaceous gland observation sample (A) is higher in speed than differentiation from an undifferentiated sebaceous gland basal cell into a mature sebaceous gland cell in a sebaceous gland of the sebaceous gland observation sample (C); and (3a) an indication that mature sebaceous gland cells that have been destroyed and are present near a central part of a sebaceous gland of the sebaceous gland observation sample (A) are larger in number of mature sebaceous gland cells that have been destroyed and are present near a central part of a sebaceous gland of the sebaceous gland observation sample (C).

An indication that the test substance has a sebum production reducing action cannot be absolutely determined because the indication varies depending on, for example, a kind of the test substance and/or a kind of a source of supply of a skin tissue for use in production of the sebaceous gland structure. Note, however, that examples of the indication include the following indications (1b) to (3b). These indications can be used alone or in combination of two or more kinds.

(1b) an indication that cells that encapsulate sebum and are located in an outermost layer of a sebaceous gland of the sebaceous gland observation sample (A) are smaller in number than cells that encapsulate sebum and are located in an outermost layer of a sebaceous gland of the sebaceous gland observation sample (C);

(2b) an indication that differentiation from an undifferentiated sebaceous gland basal cell into a mature sebaceous gland cell in a sebaceous gland of the sebaceous gland observation sample (A) is lower in speed than differentiation from an undifferentiated sebaceous gland basal cell into a mature sebaceous gland cell in a sebaceous gland of the sebaceous gland observation sample (C); and (3b) an indication that mature sebaceous gland cells that have been destroyed and are present near a central part of a sebaceous gland of the sebaceous gland observation sample (A) are smaller in number of mature sebaceous gland cells that have been destroyed and are present near a central part of a sebaceous gland of the sebaceous gland observation sample (C).

Note that the sebaceous gland observation sample (A) and the sebaceous gland observation sample (C) are merely examples. The above-described difference in dynamics of a sebaceous gland, the above-described indication that the test substance has a sebum production promoting action, and the above-described indication that the test substance has a sebum production reducing action are also referred to in another embodiment of the present evaluation method.

As described above, the present evaluation method, which makes it possible to accurately evaluate a sebum production regulating action possessed by the test substance, is expected to be used to, for example, screen sebaceous gland production regulating substances and evaluate efficacy of a sebaceous gland production regulating substance. The sebaceous gland production regulating substance is expected to be used in, for example, a sebum production reducing agent or a sebum production promoting agent to be blended with cosmetics for, for example, a facial skin, an axillary skin, and a scalp skin.

Specifically, an aspect of the present invention includes the following.

<1> A method for observing a sebaceous gland, including:

an anchoring step of anchoring a sebaceous gland structure to a support so that a sebaceous gland that is included in the sebaceous gland structure and is to be observed and the support are not in biological contact with each other, the sebaceous gland structure being obtained by removing all or part of each of dermis and hypodermis from a skin tissue; and an observation step of observing the sebaceous gland structure obtained in the anchoring step.

<2> The method recited in <1>, wherein in the anchoring step, the sebaceous gland structure is anchored to the support via at least one material selected from the group consisting of collagen, agarose, a basement membrane matrix, and poly-D-lysine.

<3> The method recited in <1> or <2>, wherein in the anchoring step, at least one tissue included in the sebaceous gland structure and selected from the group consisting of epidermis, a hair follicle, dermis, hypodermis, and a sebaceous gland different from the sebaceous gland to be observed and the support are anchored to each other.

<4> A sebaceous gland observation sample including:

a sebaceous gland structure obtained by removing all or part of each of dermis and hypodermis from a skin tissue;

a support; and an anchoring member, the sebaceous gland structure being anchored to the support via the anchoring member so that a sebaceous gland that is included in the sebaceous gland structure and is to be observed and the support are not in biological contact with each other.

<5> A test substance evaluation method for evaluating a sebum production regulating action possessed by a test substance, including:

a contact step of bringing, into contact with the test substance, a sebaceous gland observation sample recited in <4>; and an evaluation step of observing the sebaceous gland structure in the contact step so as to evaluate the sebum production regulating action of the test substance.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will more specifically discuss an aspect of the present invention with reference to Examples. Note, however, that an aspect of the present invention is not limited to such Examples. In the following description, abbreviations mean as below.

Description of Abbreviations

DMEM: Dulbecco's modified medium
FBS: fetal bovine serum
PBS: phosphate buffered physiological saline
HEPES: 4-(2-hydroxyethyl)-1-piperazine ethanesulfonic acid

[Preparation Method]

(1. Mixed Medium)

A mixed medium was obtained by adding PBS to a mixed medium of DMEM and an F-12 medium (a DMEM/F-12 medium at a volume ratio of 1:1) so that the FBS had a concentration of 10% by volume.

(2. Staining Reagent A)

A staining reagent A was obtained by adding a nucleus staining agent (trade name: hoechst 33342, manufactured by Invitrogen Corporation) to a PBS solution so that the nucleus staining agent had a concentration of 10 µg/mL.

(3. Staining Reagent B)

A staining reagent B was obtained by adding a lipid staining reagent (trade name: Nile Red, manufactured by Wako Pure Chemical Industries, Ltd.) to a PBS solution so that the lipid staining reagent had a concentration of 10 µg/mL.

(4. Preparation of Sebaceous Gland Structure)

Hypodermis was removed from a skin tissue with use of scissors under a stereoscopic microscope. Next, a sebaceous gland structure including an exposed sebaceous gland and being a quadrangle measuring approximately 3 mm to 5 mm per side was obtained by removing, with use of scissors and tweezers, a collagenous fiber from dermis of the skin tissue from which the hypodermis had been removed. Note that the sebaceous gland structure included a hair, a hair follicle, and epidermis of the skin tissue but substantially did not include dermis and hypodermis, so that the sebaceous gland was exposed.

(5. Preparation of Biological Substrate)

A collagen-containing solution A was obtained by mixing (i) 800 µL of a collagen type I-A solution (collagen type I-A content: 3% by mass, manufactured by Nitta Gelatin Inc.), (ii) 100 µL of 10×PBS (composition: 1370 mM sodium chloride, 27 mM potassium chloride, 100 mM disodium hydrogenphosphate dodecahydrate, and 18 mM potassium dihydrogenphosphate, pH 7.4), and (iii) 100 µL of a collagen reconstitution buffer (composition: 50 mM sodium hydroxide, 260 mM HEPES, and 200 mM sodium bicarbonate, pH 10.0).

Example 1

(1) Staining of Nucleus and Sebum of Sebaceous Gland Structure

The sebaceous gland structure obtained in (4. Preparation of sebaceous gland structure) above was incubated in the staining reagent A at a room temperature (25° C.) for 30 minutes, so that a nucleus of a sebaceous gland basal cell present in an outermost layer of a sebaceous gland was stained. The sebaceous gland structure subjected to staining was cleaned by being rinsed with PBS.

The sebaceous gland structure thus cleaned was incubated in the staining reagent B at a room temperature (25° C.) for 30 minutes, so that sebum included in the sebaceous gland structure was stained. The sebaceous gland structure subjected to staining was cleaned by being rinsed with PBS.

(2) Preparation of Observation Sample

The sebaceous gland structure whose nucleus and sebum had been stained was placed in a well (trade name: µ-slide 8 well, manufactured by ibidi) of an empty chamber. Subsequently, the collagen-containing solution A was dropped into the well, and the chamber was incubated at 37° C. for 5 minutes, so that both ends that were included in four ends of the sebaceous gland structure and were opposite to each other were anchored to the well of the chamber. Thereafter, 0.5 mL of a mixed medium was added to the well of the chamber to which the sebaceous gland structure had been anchored. In this case, a pair of ends of the sebaceous gland structure which ends were opposite to each other was unanchored. This allows the mixed medium to enter the sebaceous gland structure through this pair of ends and consequently allows the mixed medium to be in contact with a sebaceous gland. FIG. 2 is a view schematically illustrating a completed observation sample.

(3) Observation of Sebaceous Gland Structure

The observation sample obtained in (2) above was observed with use of a confocal laser scanning microscope for biological use (inverted microscope (trade name: IX-83, manufactured by Olympus Corporation) equipped with FV 1200 manufactured by Olympus Corporation)). The observation sample was observed from a bottom surface side of the chamber.

Approximately several ten sebaceous glands were present in a single observation sample (sebaceous gland structure measuring approximately 3 mm to 5 mm per side). A sebaceous gland present near an end of the sebaceous gland structure was expected to be in contact with the biological substrate. Thus, a single sebaceous gland present near a center of the sebaceous gland structure was to be observed. Observation was carried out, over time, while the sebaceous gland structure was being cultured under 5% $CO_2$ at 37° C. for 24 hours. FIGS. 3 to 6 each show a result of observation.

<Result>

Figure 3:
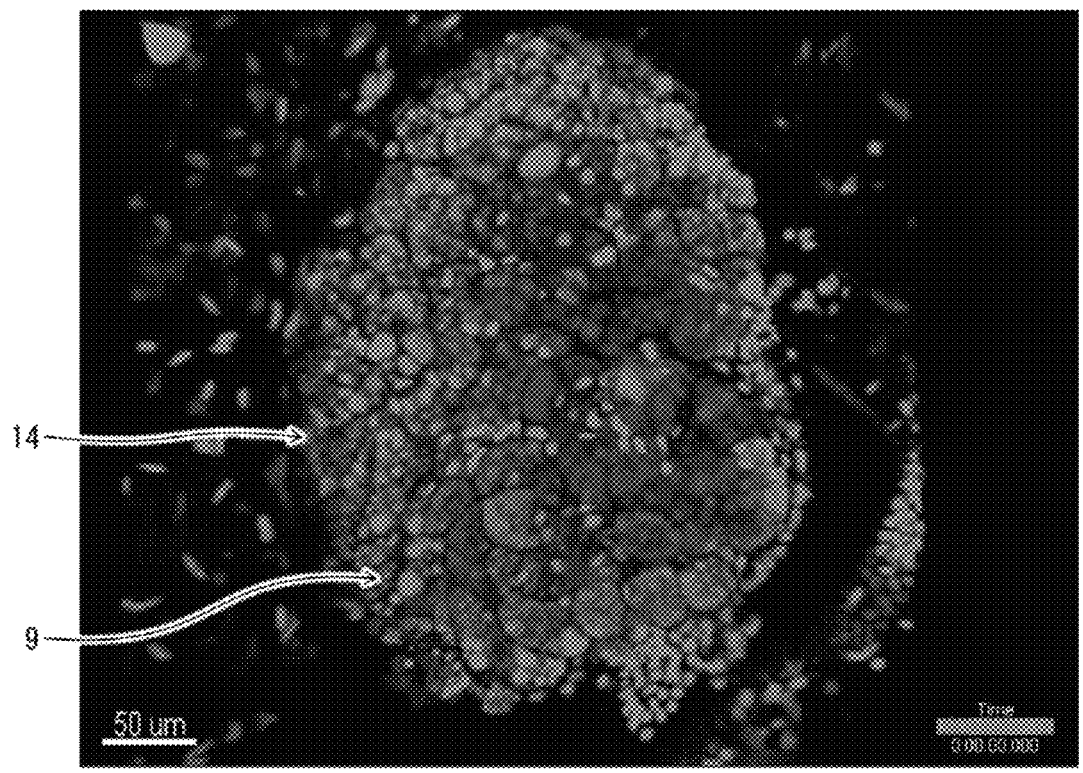
FIG. 3 is a view illustrating a result of observation of a sebaceous gland observation sample by an observation method in accordance with an embodiment of the present invention.
Figure 4:
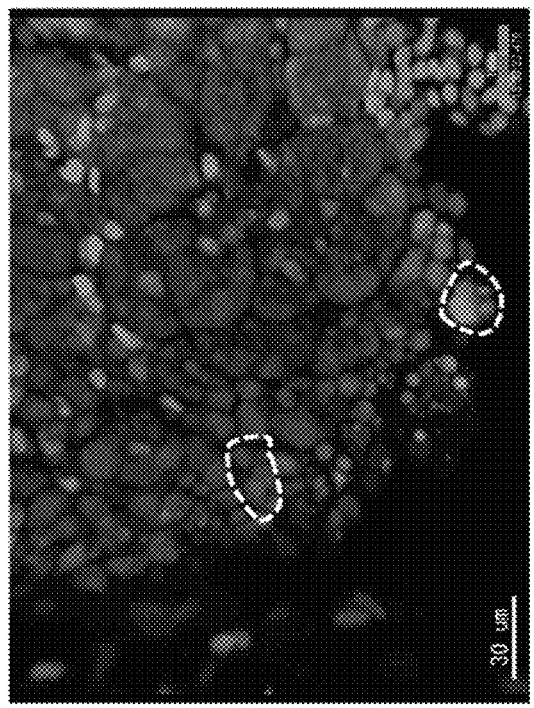
FIG. 4 is a view illustrating a result of observation of a sebaceous gland observation sample at two time points by an observation method in accordance with an embodiment of the present invention.
Figure 4:
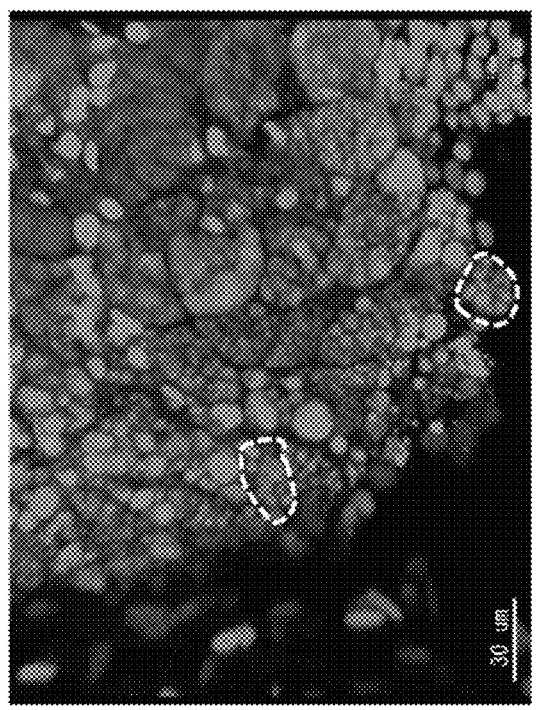
Figure 5:
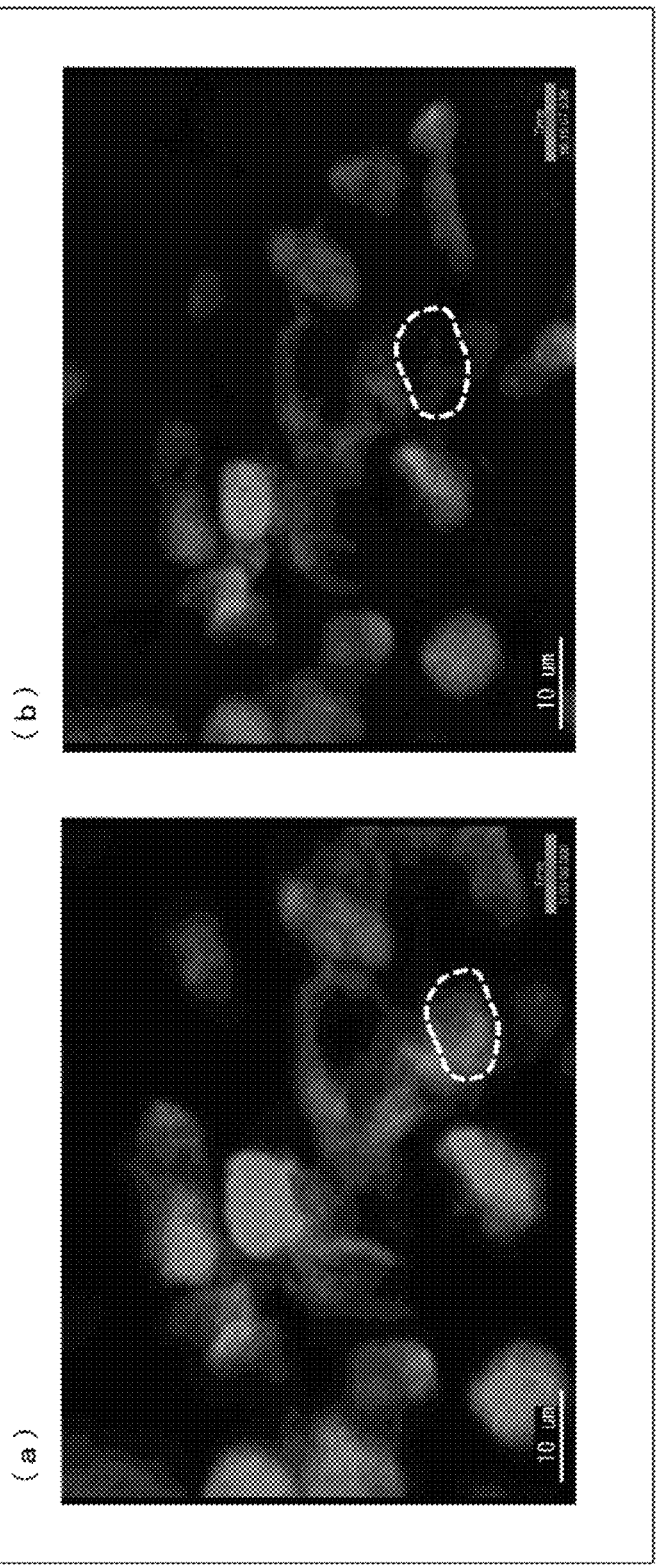
FIG. 5 is a view illustrating a result of observation of a sebaceous gland observation sample at two time points by an observation method in accordance with an embodiment of the present invention.
Figure 6:
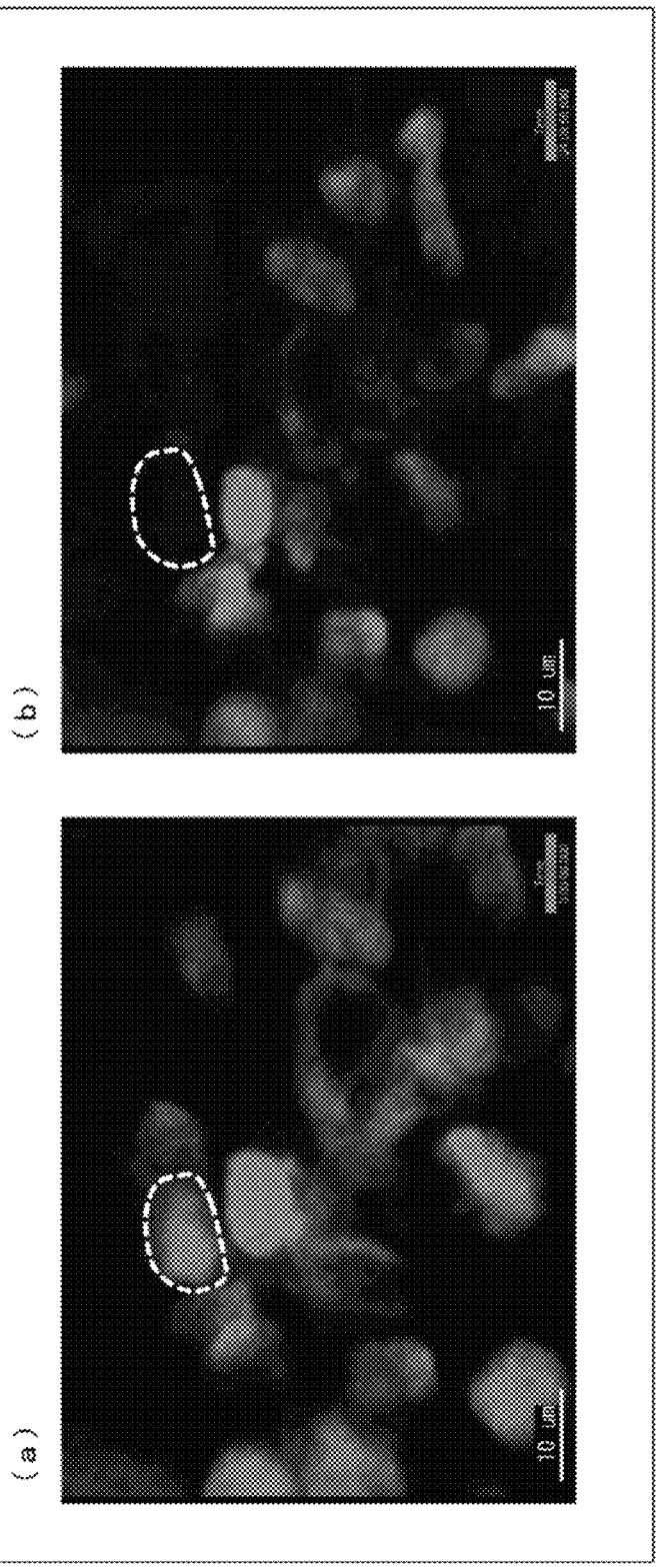
FIG. 6 is a view illustrating a result of observation of a sebaceous gland observation sample at two time points by an observation method in accordance with an embodiment of the present invention.

FIG. 3 illustrates a result of observation of a sebaceous gland at the start of observation. FIG. 4 is an enlarged view of FIG. 3. (a) of FIG. 4 illustrates a state of sebum at the start of observation, and (b) of FIG. 4 illustrates a state of sebum after an elapse of 24 hours from the start of observation. FIGS. 5 and 6 each have enlarged views of FIG. 3. (a) of each of FIGS. 5 and 6 illustrates a state of a nucleus at the start of observation, and (b) of each of FIGS. 5 and 6 illustrates a state of a nucleus after an elapse of 24 hours from the start of observation.

The result illustrated in FIG. 3 shows that no leakage of sebum was observed in the sebaceous gland structure observed. This reveals that the sebaceous gland observed was a sebaceous gland covered with a sebaceous gland basal cell and maintained an intrinsic structure of a sebaceous gland in a living body.

The result illustrated in FIG. 4 shows that sebaceous matters (i.e., sebum) that had been small were combined so as to be made larger over time. The results illustrated in FIGS. 5 and 6 show that a nucleus had disappeared over time. This reveals that the present observation method makes it possible to successively observe dynamics of each of sebum and a nucleus in a sebaceous gland. It is inferred from the results of FIGS. 4 to 6 that sebaceous matters that had been combined so as to be made larger over time ruptured a cell (caused a nucleus to disappear) and were released to an outside of the cell.

The above results show that the present observation method makes it possible to observe, over time, dynamics of a sebaceous gland which dynamics are close to dynamics of a sebaceous gland in a living body.

REFERENCE SIGNS LIST

1 Sebaceous gland structure
2 Hair
3 Hair follicle
4 Epidermis
5 Sebaceous gland
6 Sebaceous gland basal cell
7 Differentiated sebaceous gland cell
8 Mature sebaceous gland cell
9 Sebum
10 Biological substrate (anchoring member)
11 Medium
12 Support
13 Vessel
14 Nucleus
20 Sample

The invention claimed is:

1. A method for observing a sebaceous gland, comprising:
providing a sebaceous gland structure having removed all or part of dermis and all or part of hypodermis from a skin tissue, the sebaceous gland structure comprising:
a sebaceous gland,
an epidermis, wherein a lower end of the sebaceous gland being opposite to the epidermis;
an anchoring step of anchoring the sebaceous gland structure to a support such that at least a part of the lower end is unanchored to the support so that the sebaceous gland to be observed and the support are not in biological contact with each other; and
an observation step of observing the sebaceous gland structure obtained in the anchoring step.

2. The method as set forth in claim 1, wherein in the anchoring step, the sebaceous gland structure is anchored to the support via at least one material selected from the group consisting of collagen, agarose, a basement membrane matrix, and poly-D-lysine.

3. The method as set forth in claim 1, wherein in the anchoring step, at least one tissue included in the sebaceous gland structure and selected from the group consisting of epidermis, a hair follicle, dermis, hypodermis, and a sebaceous gland different from the sebaceous gland to be observed and the support are anchored to each other.

4. A sebaceous gland observation sample comprising:
a sebaceous gland structure having removed all or part of dermis and all or part of hypodermis from a skin tissue, the sebaceous gland structure comprising:
a sebaceous gland,
an epidermis, wherein a lower end of the sebaceous gland being opposite to the epidermis;
a support; and
an anchoring member,
the sebaceous gland structure being anchored to the support via the anchoring member such that at least a part of the lower end is unanchored to the support so that the sebaceous gland to be observed and the support are not in biological contact with each other.

5. A test substance evaluation method for evaluating a sebum production regulating action possessed by a test substance, comprising:
a contact step of bringing, into contact with the test substance, a sebaceous gland observation sample recited in claim 4; and
an evaluation step of observing the sebaceous gland structure in the contact step so as to evaluate the sebum production regulating action of the test substance.

\* \* \* \* \*